United States Patent
Ferguson

(10) Patent No.: US 7,115,844 B2
(45) Date of Patent: Oct. 3, 2006

(54) FLEXIBLE ELECTRIC CIRCUIT FOR HEATING COMPRISING A METALLISED FABRIC

(75) Inventor: Patrick Ferguson, N. Shields (GB)

(73) Assignee: NEL Technologies, Ltd., Newcastle upon Tyne (GB)

( * ) Notice: Subject to any disclaimer, the term of this patent is extended or adjusted under 35 U.S.C. 154(b) by 0 days.

(21) Appl. No.: 10/498,440

(22) PCT Filed: Dec. 12, 2002

(86) PCT No.: PCT/GB02/05632

§ 371 (c)(1),
(2), (4) Date: Jun. 10, 2004

(87) PCT Pub. No.: WO03/053101

PCT Pub. Date: Jun. 26, 2003

(65) Prior Publication Data

US 2005/0082280 A1    Apr. 21, 2005

(30) Foreign Application Priority Data

Dec. 14, 2001  (GB) .................................... 0129968

(51) Int. Cl.
*H05B 3/34* (2006.01)
(52) U.S. Cl. ...................... 219/549; 219/528; 338/208; 430/314
(58) Field of Classification Search ................ 219/528, 219/529, 544–549; 338/208–211, 258, 259, 338/262, 275; 427/123, 304–306; 442/231, 442/317; 174/35 MS; 430/314, 318, 323
See application file for complete search history.

(56) References Cited

U.S. PATENT DOCUMENTS

| | | | |
|---|---|---|---|
| 2,717,949 A | | 9/1955 | Challenner |
| 3,296,415 A | | 1/1967 | Eisler |
| 3,660,088 A | * | 5/1972 | Lundsager ................... 430/323 |
| 3,767,398 A | * | 10/1973 | Morgan ...................... 430/314 |
| 4,201,825 A | | 5/1980 | Ebneth |
| 4,257,176 A | | 3/1981 | Hartung et al. |
| 4,565,745 A | | 1/1986 | Kaminskas |
| 4,742,740 A | | 5/1988 | Hasslauer et al. |
| 4,798,933 A | | 1/1989 | Annovi |
| 4,948,951 A | | 8/1990 | Balzano |
| 5,352,862 A | | 10/1994 | Barr |
| 5,580,573 A | | 12/1996 | Kydonieus et al. |
| 5,648,003 A | | 7/1997 | Liang et al. |
| 5,829,171 A | | 11/1998 | Weber et al. |
| 6,227,458 B1 | | 5/2001 | Dever et al. |
| 6,229,123 B1 | * | 5/2001 | Kochman et al. ........... 219/549 |
| 6,294,313 B1 | * | 9/2001 | Kobayashi et al. ......... 430/302 |
| 6,309,986 B1 | | 10/2001 | Flashinski et al. |
| 6,551,560 B1 | | 4/2003 | Flashinski et al. |
| 2001/0002669 A1 | | 6/2001 | Kochman et al. |

FOREIGN PATENT DOCUMENTS

| | | |
|---|---|---|
| GB | 2092868 A | 8/1982 |
| GB | 2175849 A | 12/1986 |
| GB | 2205496 A | 12/1988 |

(Continued)

*Primary Examiner*—Tu Hoang
(74) *Attorney, Agent, or Firm*—Barlow, Josephs & Holmes, Ltd.

(57) ABSTRACT

A flexible electric circuit, for example an electric heater, comprises a metallised fabric (14) the metal of which is photochemically etched to form the circuit (16), the fabric preferably being porous.

10 Claims, 4 Drawing Sheets

| | FOREIGN PATENT DOCUMENTS | |
|---|---|---|
| GB | 2383197 A | 6/2003 |
| JP | 61-047686 A | 3/1986 |
| JP | 3-37021 | 2/1991 |
| JP | 4-2079 | 1/1992 |
| WO | WO 88/10058 | 12/1988 |
| WO | WO 01/01855 | 1/2001 |
| WO | WO 01/24580 A1 | 4/2001 |
| WO | PCT/TGB02/05632 | 12/2002 |
| WO | WO 03/039417 A2 | 5/2003 |
| WO | WO 03/053101 A1 | 6/2003 |
| WO | PCT/GB2004/002335 | 6/2004 |
| WO | PCT/GB2004/002346 | 6/2004 |
| WO | PCT/GB2004/002360 | 6/2004 |
| WO | PCT/GB2004/002358 | 12/2004 |

* cited by examiner

FLEXIBLE ELECTRIC CIRCUIT FOR HEATING COMPRISING A METALLISED FABRIC

TECHNICAL FIELD

This invention relates to flexible electric circuits, and has particular though not exclusive application to such circuits in the form of heaters and/or for incorporation in articles of clothing, footwear and fabric based electrical devices.

BACKGROUND OF THE INVENTION

The manufacture of flexible heaters by photochemical etching metal foil bonded to thin, flexible electrical insulation materials is a well established practice. FIG. 1a shows metal foil 2 bonded to an electrical insulation material 9 by the use of a suitable adhesive. The resulting heater element 6 and termination pads 8 shown in FIG. 1b are formed using conventional photochemical etching techniques. Leadwires 10 (FIG. 1c) are attached to the termination pads 8 by means of crimping, welding, soldering, conductive adhesives or other joining techniques. Electrical insulation is completed by bonding suitable insulation material 12 on top of the etched heater element as shown in FIG. 1d.

An alternative way to connect the leadwires 10 involves pre-forming openings in the top insulation layer 12 which is then bonded to the etched heater element 6. Subsequently, the termination pads 8 of the heater element 6 are connected to leadwires or connectors using crimping, welding, soldering, conductive adhesives or other joining techniques. The electrical insulation is completed by covering the heater element termination and leadwire joint with a patch of insulating material using an appropriate adhesive.

The electrical insulation materials used are in sheet form (up to 1 mm thick) and are typically non-porous. Common types of flexible insulating materials used are fibre reinforced silicone rubber, polyimide and polyester. Metal sheet (typically 10 μm–500 μm thick) is bonded to the insulating material using an adhesive. Metals and alloys used for heater elements typically have a resistivity which has a low dependence on temperature and include, for example, copper, nichrome, nickel and stainless steel. The resistance of the heater element, and consequently the operating temperature, is controlled by changing the type of metal foil, the thickness of the metal foil or the heater element design.

Other types of flexible heaters available utilise different forms of heating element and include wire-wound elements, interwoven carbon fibre sheets and metallised synthetic fibre sheets such as nickel coated polyester.

It is also known to utilise metallised fabrics and similar mesh structures in the manufacture of flexible heaters, for example as disclosed in GB 2,092,868 and DE 3210097. However such structures have total metallisation, and the electrical resistance is controlled by the metal composition, the density of application and the like.

SUMMARY OF THE INVENTION

It would be desirable to be able to provide a flexible electric circuit more conveniently and economically manufactured than heretofore and in which the electrical characteristics, in particular the electrical resistance, can be more easily controlled than heretofore.

According to one aspect of the present invention there is provided a flexible electric circuit comprising a metallised fabric the metal of which is photochemically etched to form the circuit.

It will be appreciated that such an arrangement is distinguished from the prior art in that the metal is modified by photochemical etching to provide circuit elements of chosen configuration and electrical properties.

Preferably the fabric is porous.

The fabric to be etched may be coated with a continuous layer of metal, for example by chemical reduction, by electro-deposition or by sputtering.

Alternatively the fabric may comprise yarns and/or fibres the individual yarns and/or fibres being encapsulated in metal prior to manufacture of the fabric.

According to a further aspect of the invention, there is provided a method of manufacturing a flexible electric circuit comprising the steps of providing a metallised fabric, and photochemically etching the metal to form the circuit.

DESCRIPTION OF PREFERRED EMBODIMENTS

Figure 1:
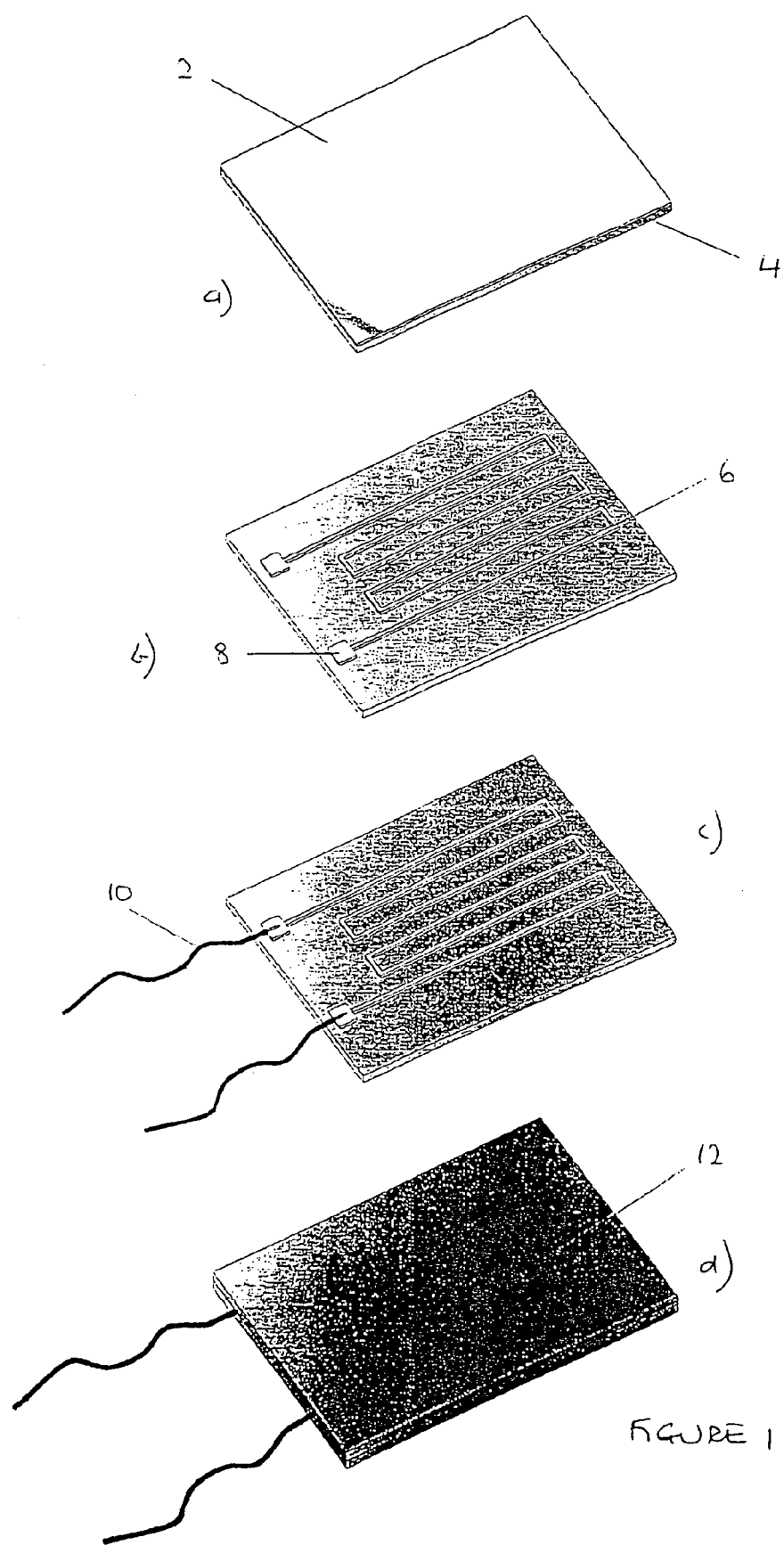
FIGS. 1a to 1d show the simplified manufacturing steps of a prior art flexible heater.
Figure 2:
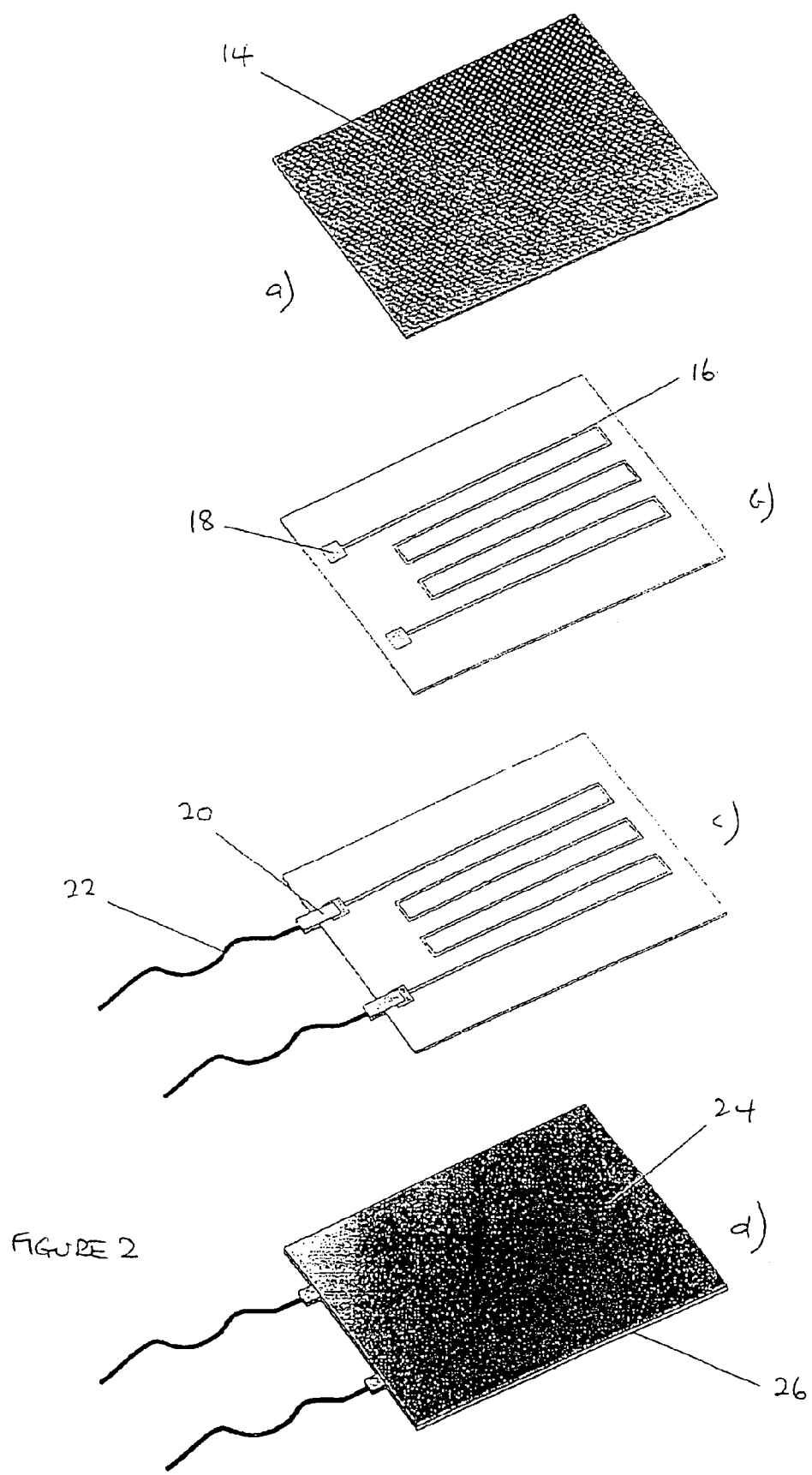
FIGS. 2a to 2d show the simplified manufacturing steps of a flexible heater according to the invention.

FIG. 2a shows a sheet of heat resistant polymeric mesh 14 coated with a continuous layer of metal and which forms the basis for a heater according to the invention.

The mesh 14 can take a variety of different configurations, a typical commercially available metallised woven polymeric mesh being Metalester™. Such products are woven electroless nickel plated polyester meshes with a variety of thread thicknesses, thread spacings, type of weave and weight of nickel. Threads may typically have a diameter within the range 24 to 600 microns, a thread count of between 4 and 737 per cm, and a metal coating of varying weight per square metre.

The fabrics may be coated with a continuous layer of metal after manufacture, for example by sputtering, by chemical reduction or by electro-deposition, which results in total encapsulation of all the threads of the mesh in metal. In an alternative mesh, the individual warp and weft threads may be metallised prior to fabric production, for example by sputtering, by chemical reduction or by electro-deposition.

The fundamental novelty of the invention is that the metallised mesh is photochemically etched to form the heater element, a typical element 16 with termination pads 18 being shown in FIG. 2b.

Crimp connectors or other suitable flexible substrate connection devices 20 are fixed to the termination pads 18 allowing leadwires 22 to be attached as shown in FIG. 2c, while electrical insulation is completed by bonding insulation material 24,26 to the top and bottom of the heater as shown in FIG. 2d.

Figure 3:
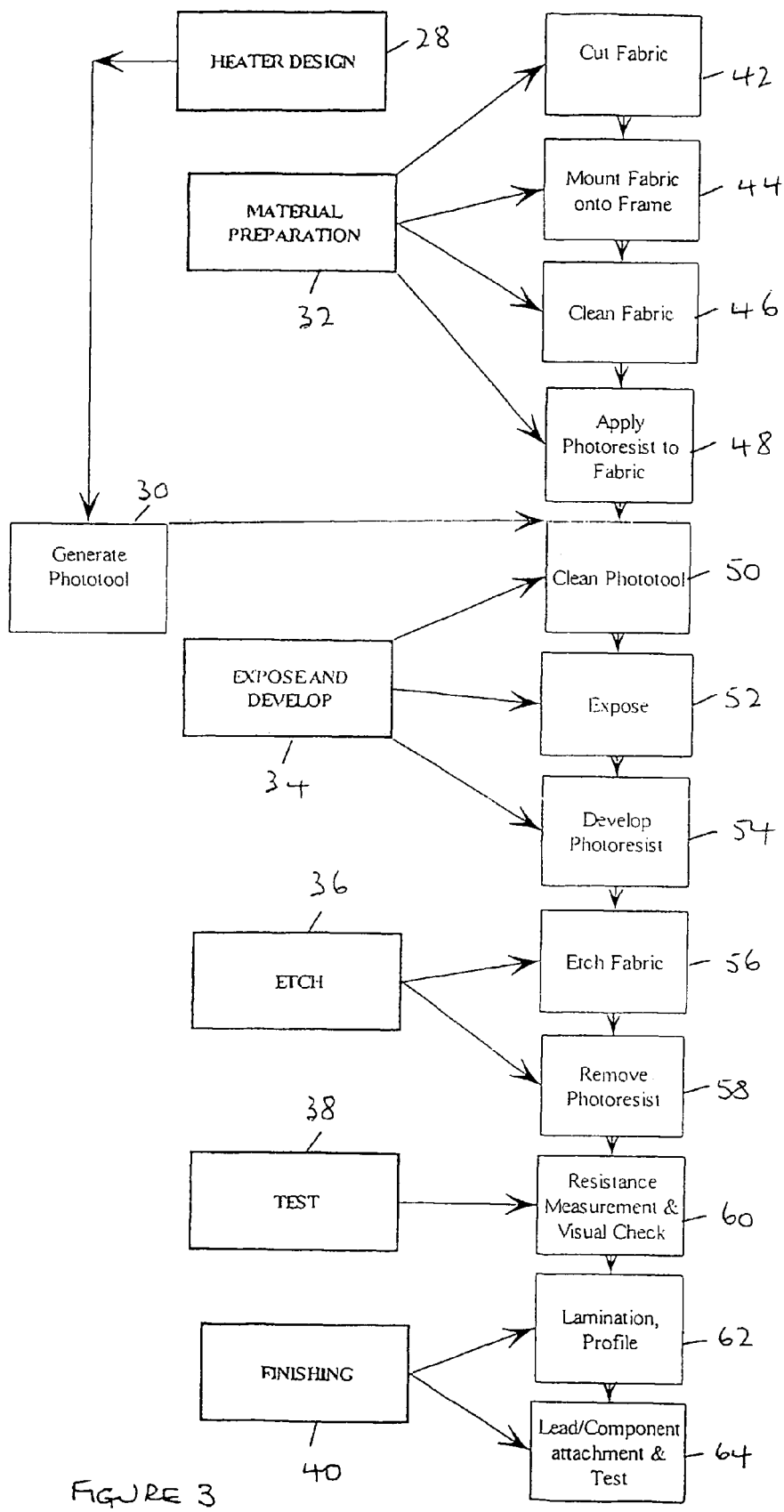
FIG. 3 is a flow chart of the manufacturing steps of a flexible heater according to the invention.

FIG. 3 shows in more detail the steps associated with the process of manufacturing an etched flexible heater from metallised woven fabric.

There are six main process steps involved, namely
1. design and generation of the phototool (boxes 28,30);
2. material preparation (box 32);

3. exposure and developing (box 34)
4. etching (box 36)
5. testing (box 38)
6. finishing (box 40).

The material preparation step 32 is divided into the sub-steps of:

a) cutting the metallised fabric to length (box 42);
b) mounting the cut fabric onto a hinged frame (box 44), typically 1.5 mm thick brown styrene board, to enable the otherwise flimsy fabric to be more readily handled and to travel flat through the subsequent multi-stage manufacturing process;
c) cleaning the fabric with a commercial surface cleaning agent (box 46) to assist the adhesion of the photoresist—if the cleaning agent is not used, and the surface is contaminated, there is a tendency for poor adhesion of the photoresist to the metal to be etched which can result in the etchant undercutting the photoresist and attacking the metal area which forms the required image, in turn reducing the track width and increasing the resistance of the track;
d) applying the photoresist (box 48)—one method of applying the photoresist is by dip-coating—i.e. immersing the fabric in a liquid photoresist to ensure a controlled application of liquid photoresist to all parts of the metallised polyester threads and to avoid undercutting of the etched track due to non-application of photoresist to parts of the threads.

The exposure and developing step 34 is divided into the sub-steps of:

a) cleaning the phototool (box 50);
b) exposing the photoresist to ultraviolet light (box 52), and
c) developing the image of the heater element on the fabric (box 54).

The etching step 36 is divided into the sub-steps of:

a) progressively etching away the unrequired metal (box 56), and
b) removing the photoresist to leave the required heater element (box 58).

The resultant flexible heater is then tested, for example by measuring the electrical resistance, and by visual inspection (box 60).

The heater is finished by electrically insulating the porous woven metallised etched fabric, for example by bonding layers of suitable electrically insulating sheet material to each side using a web consisting of low melt fibres—adhesive in the open mesh area can be minimised by applying a vacuum during lamination—or by dip-coating or paint-spraying the etched fabric with a suitable heat resistant lacquer—again the use of a vacuum after lacquer application will maximise the mesh open area. To further improve the porosity of the heater, the laminated insulating material may be a micro-porous breathable fabric or film. After lamination, the porous heater is profiled by cutting to its final shape (box 62).

The attachment of leadwires and other components such as thermal protection devices complete the product which is then re-tested for electrical performance (box 64).

Clearly the desired electrical characteristics of a heater, and in particular the heat output, will determine the particular metallised woven fabric to be used to manufacture the heater, and the width and length of the element to be photochemically etched on the fabric.

Figure 4:
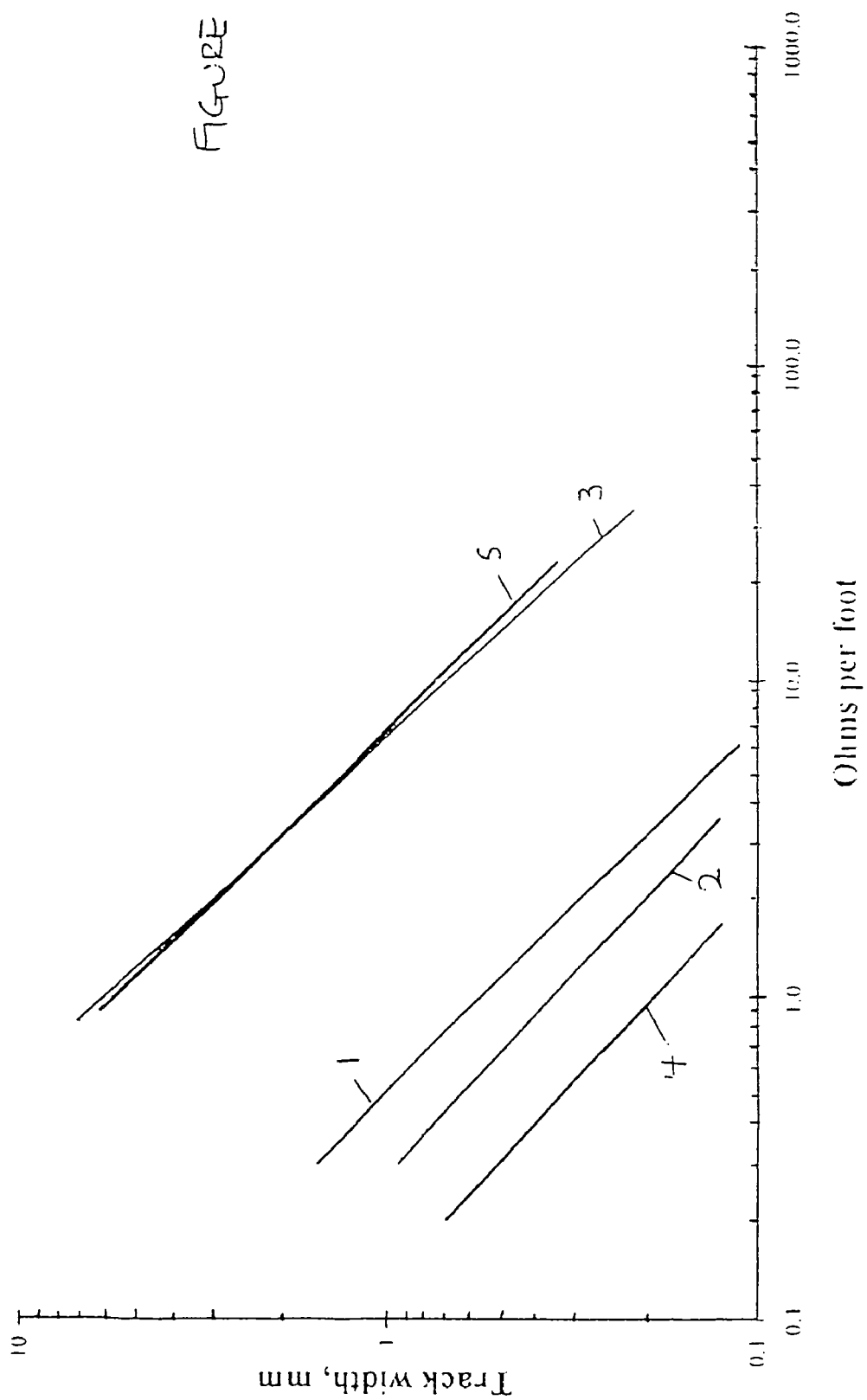
FIG. 4 is a graph showing the log of the resistance change against track width for a standard element design for various metal foil heater elements and for the element of a heater according to the invention.

FIG. 4 shows a graph of the log of the track width in mm against the log of the resistance of the track in ohms per foot for a standard element design for each of four conventional etched foil heaters and a heater according to the invention.

The individual graphs in FIG. 4 are:
1. annealed nickel foil of 50 microns thickness;
2. annealed copper foil of 18 microns thickness;
3. annealed stainless steel (Grade 321) of 38 microns thickness;
4. annealed copper foil of 35 microns thickness;
5. Metalester™ MET 25/16 (25 g.m$^{-2}$).

It can be seen that product 5, a heater according to the invention, has a resistance substantially the same as that of the stainless steel foil heater 3.

More particularly, the metal, the fibre diameter, the thickness of the metal coating, the spacing of the fibres and the element design are all taken into account to determine the required electrical characteristics.

In the above described example, the threads are typically polymeric, particularly polyester for relatively low temperature applications, although any synthetic or natural fibres may suffice as a base for the product of the invention.

In the invention the flexible electric circuit may be manufactured from fabrics incorporating yarns of the following two classes:

(i) Continuous: mono or multi-filaments of indefinite length and including polypropylene, polyethylene, chlorofibres, viscose rayon, di- and tri-acetate, polyester, nylon, aromatic polyamide (Nomex®), poly-par-aphenylene terephthalamide (Kevlar®), and the like. Nomex® and Kevlar® are registered trademarks of E.I. du Pont de Nemours and Company.

(ii) Staple: fibres of definite length twisted, wrapped or otherwise combined, including cotton, linen (flax), jute, wool, mohair, cashmere, angora and other speciality hair fibres, blends of varying composition thereof e.g. 60% cotton/40% polyester and the like.

Fabrics made from the above yarns or fibres (depending on the type of fabric structure) include and are not limited to the following types:
(i) woven
(ii) nonwoven
(iii) knitted—includes warp and weft
(iv) composites—laminated structures incorporating but not limited to the following: textiles, coatings, polymer films, membranes, hydrophilic and micro-porous breathable films, metals, ceramics and other materials.
(v) pressed felts
(vi) braids.

The metal is conveniently nickel, although any resistive metal could be used.

The resultant product is thin, flexible and porous, and can be produced relatively inexpensively.

Flexible heaters according to the invention and in the form of photochemically etched metallised fabric mesh have a variety of applications, and can be incorporated in, for example, mosquito traps, wound care products such as medical bandages and dressings, surgical masks and visors, motorcycle visors, sports equipment visors, outdoor and performance clothing, footwear and articles to be moulded, and can be used as aerospace de-icers. Other applications will be apparent to those skilled in the art.

Although described above as heaters, the invention is equally applicable to flexible electric circuits for use other than as heaters.

Such a circuit is photochemically etched from metallised woven fabric as detailed above with respect to the heater element 16, and any additional components that are required are mounted thereon. Such a thin, flexible, porous electric circuit can be embedded into articles of wearable clothing and footwear, for example outdoor and performance clothing, military clothing, medical and sports garments, ski and walking boots, trainers, or be incorporated into other products to enhance their functionality and to enable the control of associated electrical equipment, for example, computers; computer keyboards; telephones; mobile telephones; personnel data organisers; computer mouse; personnel audio; global positioning systems; domestic appliances; TV/videos; hi-fi and music systems; computer game consoles; electronic musical instruments; toys; lighting; clocks and watches; mosquito traps; personal healthcare products including heart rate and other vital sign monitors, disability and mobility aids; automotive user controls; sports equipment; ski goggles; skis; crash helmets for motorcycles, scooters, bikes, snow sports, motor sports, water sports; sports braces; controls for wearable electronics; educational aids; medical applications such as bed pads and blankets; medical sensors; blood and glucose monitoring sensors and personal protection devices (including alarm systems).

The invention claimed is:

1. A flexible electric circuit comprising a metallised substrate of porous fabric having a plurality of components each encapsulated with metal, wherein the metal on the metallised substrate of fabric is photochemically etched to form the circuit by selectively etching out metal encapsulated about the plurality of components of the substrate of porous metallised fabric.

2. The circuit of claim 1, wherein the components of the substrate of porous metallised fabric are individual yarns, the individual yarns being encapsulated in metal after manufacture of a substrate of a porous fabric to form the substrate of porous metallised fabric.

3. The circuit of claim 1, wherein the components of the substrate of porous metallised fabric are individual fibres, the individual fibres being encapsulated in metal after manufacture of a substrate of a porous fabric to form the substrate of porous metallised fabric.

4. The circuit of claim 1, wherein the components of the substrate of porous metallised fabric are individual yarns, the individual yarns being encapsulated in metal prior to manufacture of the substrate of porous metallised fabric.

5. The circuit of claim 1, wherein the substrate of porous metallised fabric is selected from the group consisting of woven, non-woven, knitted, laminated composite, pressed felt, and braid fabrics.

6. The circuit of claim 1, wherein the components of the substrate of porous metallised fabric are woven polyester threads and the metal is nickel.

7. The circuit of claim 1, wherein the components of the substrate of porous metallised fabric are individual fibres, the individual fibres being encapsulated in metal prior to manufacture of the metallised fabric substrate.

8. A method of manufacturing a flexible circuit comprising the steps of:
providing a substrate of porous metallised fabric having a plurality of components each encapsulated with metal; and
photochemically etching the metal encapsulated about the components of the substrate of porous metallised fabric to form the circuit by selectively etching out the metal encapsulated about the components of the substrate of porous metallised fabric.

9. The method of claim 8, further including the step of:
applying a liquid photoresist to the metal encapsulated about the components of the substrate of porous metallised fabric so that the liquid photoresist is applied to all parts of the substrate of porous metallised fabric.

10. The method of claim 9, wherein the liquid photoresist is applied to the substrate of porous metallised fabric by dipcoating of the substrate of porous metallised fabric into the liquid photoresist.

* * * * *